(12) United States Patent
Gunderson

(10) Patent No.: US 7,641,647 B2
(45) Date of Patent: Jan. 5, 2010

(54) MEDICAL DEVICE WITH MODIFIED MARKER BAND

(75) Inventor: Richard C. Gunderson, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 553 days.

(21) Appl. No.: 10/749,499

(22) Filed: Dec. 29, 2003

(65) Prior Publication Data

US 2005/0148866 A1   Jul. 7, 2005

(51) Int. Cl.
*A61M 25/098* (2006.01)
(52) U.S. Cl. ........................ 604/529; 600/435
(58) Field of Classification Search ............. 604/103.1, 604/96.01, 93.01, 48, 19, 529, 528, 523, 604/264; 600/431, 407, 300, 435, 434
See application file for complete search history.

(56) References Cited

U.S. PATENT DOCUMENTS

| | | | |
|---|---|---|---|
| 4,041,931 A | | 8/1977 | Elliott et al. |
| 4,419,095 A | * | 12/1983 | Nebergall et al. ........ 604/103.1 |
| 4,763,647 A | | 8/1988 | Gambale |
| 4,938,220 A | * | 7/1990 | Mueller, Jr. ................. 600/435 |
| 5,024,232 A | * | 6/1991 | Smid et al. .................. 600/431 |
| 5,034,005 A | * | 7/1991 | Appling ....................... 604/529 |
| 5,045,071 A | * | 9/1991 | McCormick et al. ........ 604/529 |
| 5,253,653 A | | 10/1993 | Daigle et al. |
| 5,300,048 A | * | 4/1994 | Drewes et al. ............... 604/529 |
| 5,368,048 A | | 11/1994 | Stoy et al. |
| 5,429,597 A | | 7/1995 | De Mello et al. |
| 5,429,617 A | | 7/1995 | Hammersmark et al. |
| 5,484,425 A | * | 1/1996 | Fischell et al. .............. 604/528 |
| 5,549,552 A | | 8/1996 | Peters et al. |
| 5,558,652 A | * | 9/1996 | Henke ......................... 604/529 |
| 5,606,981 A | * | 3/1997 | Tartacower et al. ......... 600/585 |
| 5,724,989 A | * | 3/1998 | Dobson ....................... 600/585 |
| 5,725,572 A | * | 3/1998 | Lam et al. ................... 623/1.16 |
| 5,759,174 A | | 6/1998 | Fischell et al. |
| 5,772,609 A | | 6/1998 | Nguyen et al. |
| 5,836,892 A | * | 11/1998 | Lorenzo ...................... 600/585 |
| 5,846,199 A | * | 12/1998 | Hijlkema et al. ............ 600/435 |
| 5,908,413 A | * | 6/1999 | Lange et al. ................. 604/529 |
| 5,921,978 A | | 7/1999 | Thompson et al. |
| 5,948,489 A | * | 9/1999 | Hopkins ...................... 428/34.9 |
| 6,036,682 A | * | 3/2000 | Lange et al. ................. 604/529 |
| 6,139,510 A | | 10/2000 | Palermo |
| 6,179,811 B1 | | 1/2001 | Fugoso |
| 6,210,396 B1 | * | 4/2001 | MacDonald et al. ........ 604/529 |
| 6,277,108 B1 | * | 8/2001 | McBroom et al. ........... 604/529 |
| 6,285,903 B1 | * | 9/2001 | Rosenthal et al. ........... 600/433 |

(Continued)

FOREIGN PATENT DOCUMENTS

EP   0 303 487 A2   2/1989

*Primary Examiner*—Nicholas D Lucchesi
*Assistant Examiner*—Theodore J Stigell
(74) *Attorney, Agent, or Firm*—Crompton, Seager & Tufte, LLC

(57) ABSTRACT

A marker band and medical devices such as catheters and guidewires that include a marker band. A marker band may include a generally cylindrical body portion having one or more slots or openings defined therein. The marker band is configured for being secured to a medical device. Methods of making and using a marker band and a medical device having a marker band are also disclosed.

18 Claims, 4 Drawing Sheets

U.S. PATENT DOCUMENTS

| | | | |
|---|---|---|---|
| 6,520,934 B1 * | 2/2003 | Lee et al. | 604/103.1 |
| 6,540,721 B1 | 4/2003 | Voyles et al. | |
| 6,733,489 B2 * | 5/2004 | Nutting et al. | 604/529 |
| 6,945,956 B2 * | 9/2005 | Waldhauser et al. | 604/95.01 |
| 6,949,114 B2 * | 9/2005 | Milo et al. | 606/213 |
| 6,970,734 B2 * | 11/2005 | Eidenschink et al. | 600/424 |
| 2002/0095205 A1 | 7/2002 | Edwin et al. | |
| 2002/0156460 A1 * | 10/2002 | Ye et al. | 604/534 |
| 2003/0121148 A1 * | 7/2003 | DiCaprio | 29/890.09 |
| 2003/0125711 A1 | 7/2003 | Eidenschink et al. | |
| 2005/0148866 A1 * | 7/2005 | Gunderson | 600/431 |
| 2005/0255317 A1 * | 11/2005 | Bavaro et al. | 428/375 |

\* cited by examiner

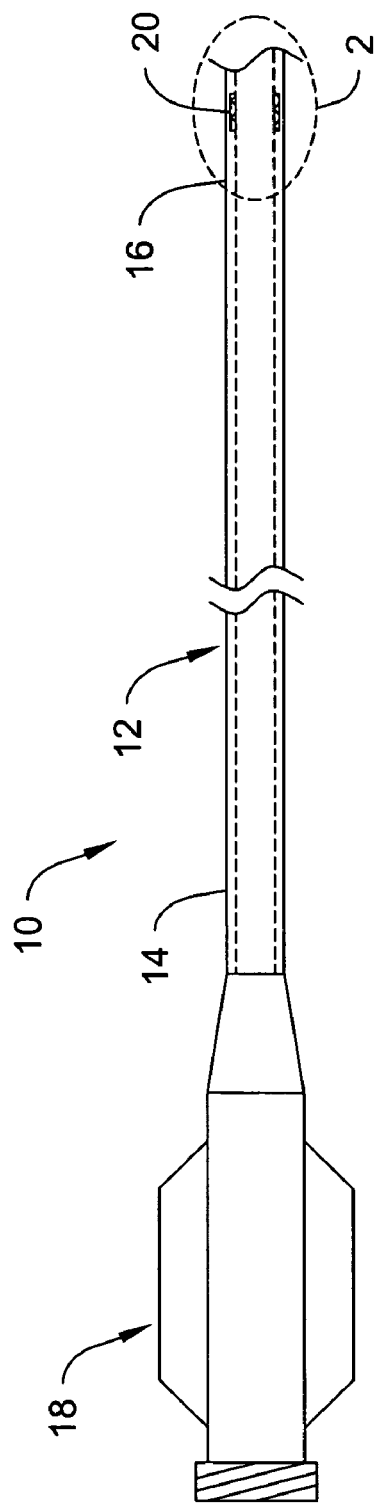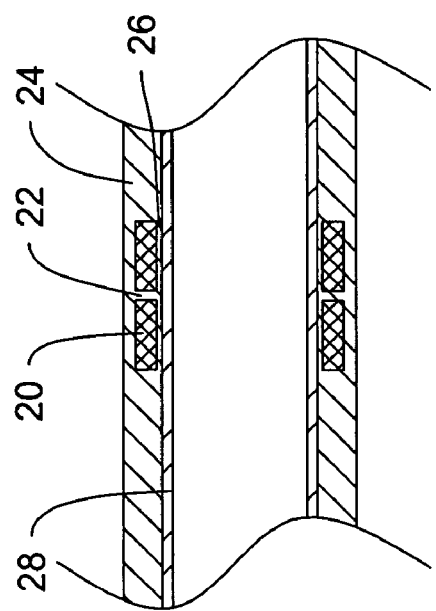

US 7,641,647 B2

MEDICAL DEVICE WITH MODIFIED MARKER BAND

FIELD OF THE INVENTION

The present invention pertains to marker bands for in-vivo radiographic visualization and medical devices that include a marker band. More particularly, the present invention pertains to marker bands that include one or more holes or slots defined therein and medical devices that include these modified marker bands with polymeric material filling the holes or slots.

BACKGROUND OF THE INVENTION

A wide variety of radiopaque marker bands have been developed for intracorporal medical devices. Some of the devices that include marker bands are guidewires and catheters. Of the known marker bands and intracorporal medical devices witzh marker bands, each has certain advantages and disadvantages. There is an ongoing need to provide alternative designs and methods of making and using marker bands and medical devices with marker bands.

SUMMARY OF THE INVENTION

The invention provides design, material and manufacturing method alternatives for radiopaque marker bands, and medical devices with marker bands. In at least some embodiments, the marker bands include a body region having one or more holes or slots formed therein. The holes may desirably impact the bonding between the marker band and a catheter shaft or other suitable structure. These and some of the other features and characteristics of example embodiments are described in more detail below.

BRIEF DESCRIPTION OF THE DRAWINGS

FIG. 1 is a partial cross-sectional side view of an example medical device having a marker band;

FIG. 2 is a cross-sectional side view of a portion of the medical device shown in FIG. 1;

DETAILED DESCRIPTION OF THE PREFERRED EMBODIMENTS

Figure 3:
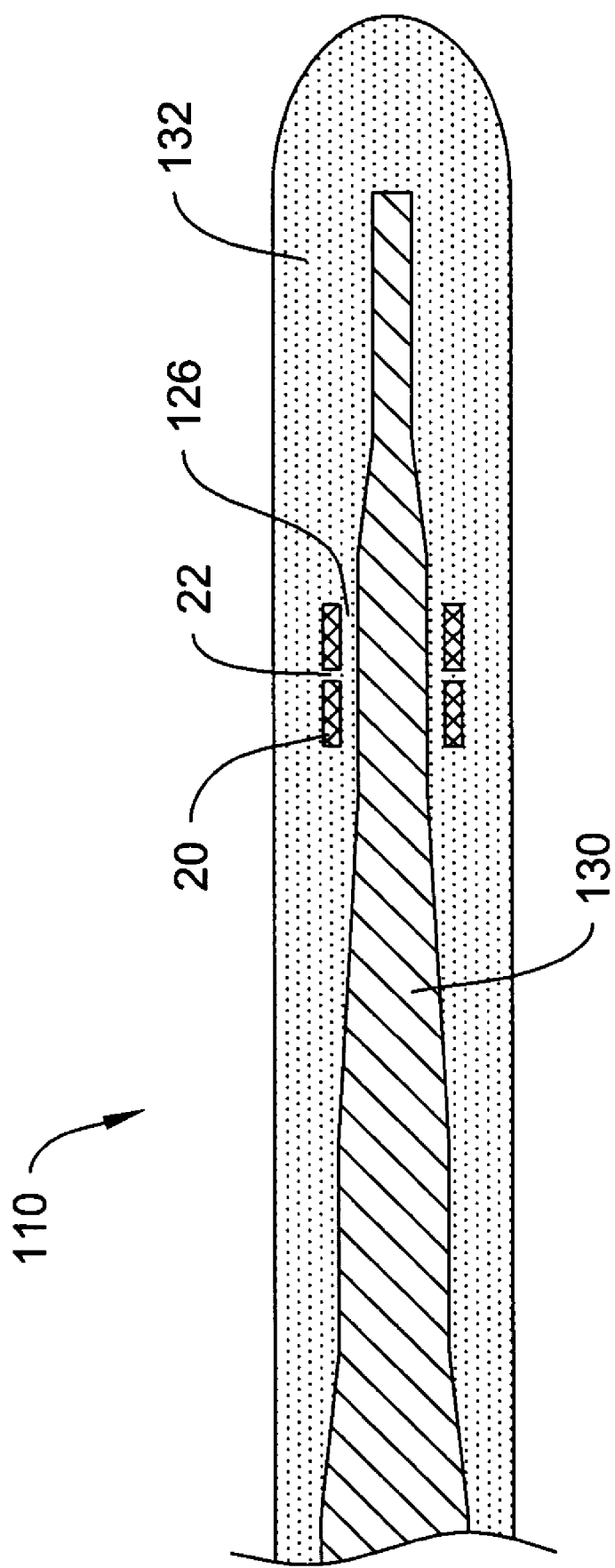
FIG. 3 is a cross-sectional side view of another example medical device having a marker band.

The following description should be read with reference to the drawings wherein like reference numerals indicate like elements throughout the several views. The detailed description and drawings illustrate example embodiments of the claimed invention.

FIG. 1 is an example medical device 10, generally depicted as a guide catheter. Catheter 10 may include an elongate catheter shaft 12 having a proximal end region 14 and a distal end region 16. A hub 18 may be coupled to proximal end region 14. Example guide catheters include a tubular lubricious liner that forms a lumen therein. In many embodiments, a reinforcing member extends over the liner for a selected distance from the proximal end to provide stiffness. The reinforcement can be a metallic braid or other means known in the art. An outer polymeric layer generally extends over the braid and inner tubular member. Catheter 10 may also include one or more marker bands 20. Marker bands 20 may be disposed at essentially any position along shaft 12. Although medical device 10 is depicted in FIG. 1 as a guide catheter, device 10 could be any other type of catheter including diagnostic or therapeutic catheters such as angioplasty balloon catheters, atherectomy catheters, stent delivery catheters, and the like, or any other suitable device. Furthermore, medical device 10 can generally include any device designed to pass through an opening or body lumen. For example, medical device 10 may comprise an endoscopic device, laproscopic device, embolic protection device, guidewire (as shown in FIG. 3), and the like, or any other suitable device.

Generally, the purpose for including marker band 20 as a part of catheter 10 or any other medical device is to aid in the visualization of catheter 10 (via any number of known visualization techniques) while the medical device is in use within the body. Typically the visualization techniques used rely on marker band 20 being made from or otherwise including a radiopaque material. Radiopaque materials are understood to be materials capable of producing a relatively bright image on a fluoroscopy screen or another imaging technique during a medical procedure. This relatively bright image aids the user of catheter 10 in determining its location. Some examples of radiopaque materials can include, but are not limited to, gold, platinum, platinum-iridium, palladium, tantalum, tungsten alloy, plastic material loaded with a radiopaque filler, and the like.

Marker band 20 may be incorporated into catheter 10 by disposing marker band 20 over catheter shaft 12 during the manufacturing process. This manufacturing step may also include securing the position of marker band 20 relative to shaft 12. Securing the position of marker band 20 may be important for a number of reasons. For example, if marker band 20 is properly secured, the clinician can rely on the known position of marker band 20 in order to accurately assess the position of the remainder of catheter 10. This may include the clinician being able to know the precise location of the distal end of catheter 10 by virtue of visualizing marker band 20 and knowing how far marker band 20 is from the distal end of catheter 10. This may be critically important when catheter 10 is being used in a particular sensitive location, such as the central nervous system, because errantly positioning the catheter 10 could damage sensitive areas. It can be appreciated that given the small scale of catheters and blood vessel, even a very small shift in the position of marker band 20 can have real impact on a medical intervention.

Marker band 20 may include a number of refinements, which may provide a number of desirable features to catheter 10 and/or marker band 20 itself. These refinements may include improving the bonding between marker band 20 and shaft 12. For example, marker band 20 may include one or more holes or slots 22 formed therein, as shown in FIG. 2. Here it can be seen that holes 22 may improving the bonding of marker band 20 to shaft 12, for example, by interlocking marker band 20 with shaft 12 by including an exterior polymer layer 24. Interlocking may be accomplished by disposing polymer layer 24 over marker band 20, then melting and allowing polymer layer 24 to flow through holes 22 and within the space or void 26 that may exist between marker band 20 and an inner liner or shaft portion 28. Therefore, including slits 22 allows for consistent and predictable reflow of polymer layer 24 that essentially fills space 26. Once the polymer layer 24 is solidified or otherwise hardened, marker band 20 becomes locked into position. As described above, securing the position of marker band 20 may be desirable.

The manufacturing steps that can be used to create the interlocking structure or arrangement between marker band 20 and shaft 12 may include extruding polymer layer 24 over marker band 20 and liner 28. Liner 28 may comprise a generally tubular shaft that may be made of a metal, metal alloy, polymer, composite material, and the like, or any other suitable material. For example, liner 28 may comprise a stainless steel or nickel-titanium alloy hypodermic tube (i.e., a "hypotube"), a polytetrafluoroethylene (PTFE) liner or etched PTFE liner, or any other suitable structure. During the extrusion, polymer layer 24 may be suitably molten or sufficiently adapted to flow through holes 22 and into space 26. Alternatively, polymer layer 24 can become disposed within holes 22 and space 26 by heating polymer layer 24 as a part of the extrusion or in a separate manufacturing methodology. It can be appreciated that a number of other manufacturing methods may be substituted that generally result in an exterior layer becoming disposed over marker band 20, within holes 22, and under marker band 20 (i.e., between marker band 20 and liner 28).

Including marker band 20 with holes 22 may be desirable for a number of other reasons. For example, holes 22 may allow for less material to be used for securing marker band 20 to shaft 12 (and/or liner 28). Accordingly, catheter 10 can be manufactured with a decreased outer profile. Reducing the amount of material used may also increase the flexibility, which may be desirable. In addition, if spaces 26 are formed during the manufacturing process (which can be the case in medical devices that do not include marker band 20) the outer surface of the medical device may form a corresponding outward projection or "bump". This may create an uneven outer surface that may not be desirable. Therefore, the use of marker band 20 may reduce the prevalence of these "bumps". Moreover, the use of marker band 20 may reduce the amount of manufacturing steps required to build catheter 10, which can simplify the manufacturing process and can reduce manufacturing costs.

FIG. 3 depicts another example medical device 110, this time the distal portion of a guidewire, in order to illustrate that marker band 20 may be used with essentially any other suitable medical device including a guidewire. Guidewire 110 is similar to typical guidewires and may include a central core wire 130 and a polymer jacket 132 disposed over core wire 130. Marker band 20 may be disposed over core wire 130. Polymer jacket 132 may flow through holes 22 in marker band 20 so as to fill space 126 (which is shown larger than it would likely be in practice) and secure marker band 20.

Figure 4:
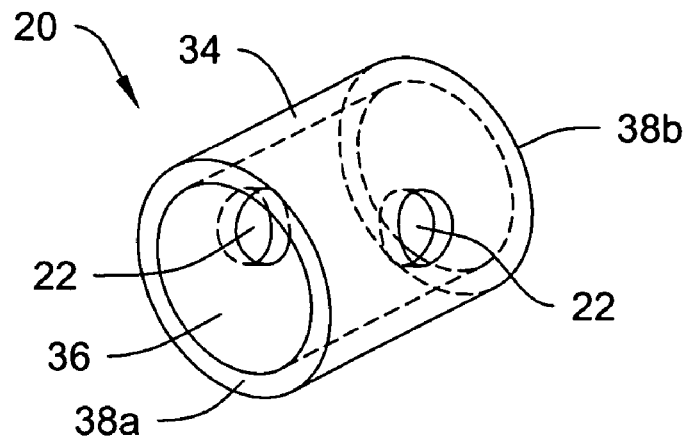
FIG. 4 is a perspective view of an example marker band for use with a medical device.

FIGS. 4-9 illustrate a number of different forms of marker band 20 that are contemplated. For example, FIG. 4 depicts marker band 20. The general form of marker band 20 and the others described below is that they include a generally tubular or cylindrical body portion 34 defining a central channel 36 and a pair of opposing ends 38*a/b*. Holes 22 are formed within body portion 34 and generally extend all the way through body portion 34 and into channel 36 so that materials (e.g., polymer layer 24) can flow therethrough and into channel 36. As described above, marker band 20 is made from or otherwise includes a radiopaque material.

Similarly to what is described above, marker band 20 can be disposed over liner 28 (or any other portion of shaft 12) by sliding marker band 20 thereover to the desired position. In some embodiments, the desired position for marker band 20 is near the distal end of the device. However, marker band 20 can be disposed at essentially any position along shaft 12. Moreover, any number of marker bands 20 may be used, such as 1, 2, 3, 4, 5, 6, or more marker bands. If it is not practical to slide marker band 20 over shaft 12, it may be desirable to form marker band 20 from a generally flat or planar sheet of material and then wrap the material into a generally cylindrical shape (or any other suitable shape) about shaft 12. Typically there will be a relatively tight tolerance between marker band 20 and shaft 12.

Once properly positioned, polymer layer 24 can be disposed over marker band 20. As described above, polymer layer 24 can flow through holes 22 and fill any void 26 that might otherwise be created between marker band 20 and shaft 12. Accordingly, it may be desirable to use a thermoplastic material (i.e., a material whose viscosity changes with the induction of heat), a thermoplastic-like material, a thermoset material, combinations thereof, or the like for polymer layer 24. Some examples of suitable polymers (including thermoplastics) may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, polyethylene (PE), Marlex high-density polyethylene, Marlex low-density polyethylene, linear low density polyethylene (for example, REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, perfluoro(propyl vinyl ether) (PFA), low durometer thermal plastics (e.g., 25-50 Sure D), tungsten loaded thermal plastic compound, bismuth subcarbonate loaded thermal plastic compound, barium sulfate loaded thermal plastic compound, other suitable materials, or mixtures, combinations, copolymers thereof, polymer/metal composites, and the like. In some embodiments, polymer layer 24 can be blended with a liquid crystal polymer (LCP). For example, the mixture can contain up to about 5% LCP. In some embodiments, polymer layer 24 may include multiple segments of polymeric material having desired property variations.

Alternatively, polymer layer 24 may be or include a coating, for example, a lubricious, a hydrophilic, a protective, or other type of coating may be applied over portions or all of shaft 12 or other portions of catheter 10. Hydrophobic coatings such as fluoropolymers provide a dry lubricity which improves catheter and guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

Figure 5:
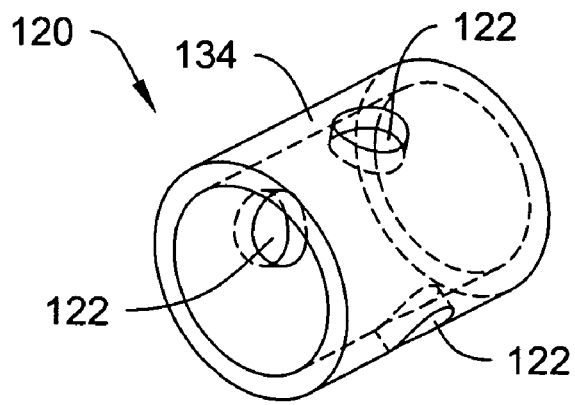
FIG. 5 is a perspective view of another example marker band for use with a medical device.

FIG. 4 shows that marker band 20 may include two holes 22. However, this need not be the case as other numbers are contemplated. For example, FIG. 5 depicts marker band 120 that includes three holes 122 formed therein. It can also be seen that the arrangement of holes 122 can also vary. For example, holes 122 are arranged in a staggered configuration about body portion 134 of marker band 120. The staggered configuration is understood to be an arrangement where no two holes 122 are radially aligned.

Figure 6:
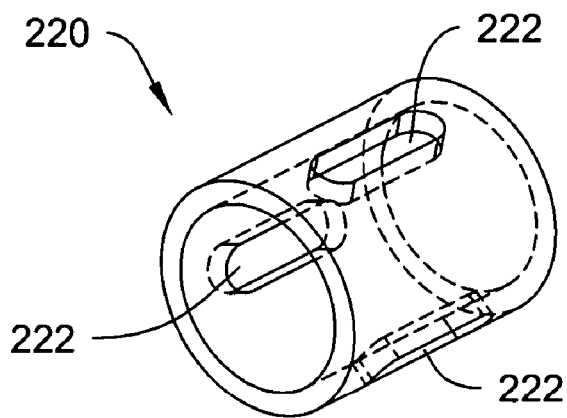
FIG. 6 is a perspective view of another example marker band for use with a medical device.

The shape of the holes defined in the various marker bands may also vary. For example, FIGS. 4 and 5 depict holes 22/122 as being generally circular. This is not intended to be limiting, as any suitable shape may be utilized without departing from the spirit of the invention. For example, FIG. 6 shows marker band 220 having oval or pill-shaped holes 222. It can be appreciated that holes 222 may alternatively be triangular, squared, rectangular, polygonal, irregularly shaped, and the like, or have combinations of these or any other shape.

Figure 7:
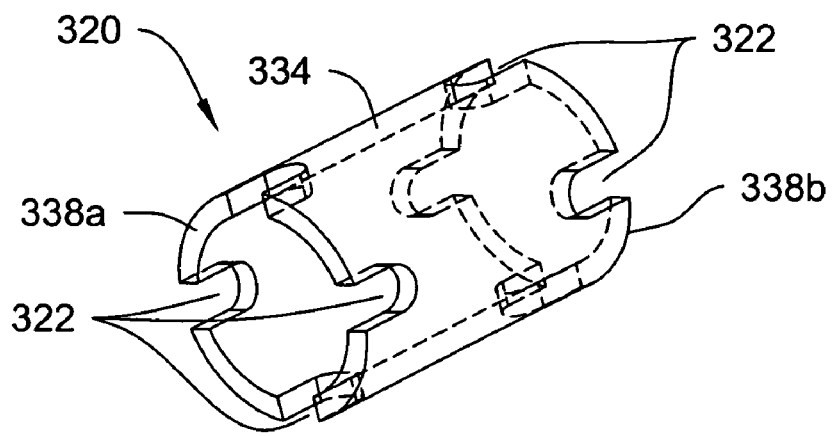
FIG. 7 is a perspective view of another example marker band for use with a medical device.

FIG. 7 is another example marker band 320 where holes or slits 322 are disposed at the ends 338a/b of body portion 334. Holes or slits 332 may be defined by, for example. one or more longitudinal deflections defined in ends 338a/b of body portion 334. This embodiment illustrates tat slits 322 can be disposed at essentially any position along marker band 320 and still have the desired effects. For example, slits 322 disposed at ends 338a/b allow polymer layer 24 to flow under marker band 320 so as to improve bonding between marker band 320 and shaft 12, as described above.

Figure 8:
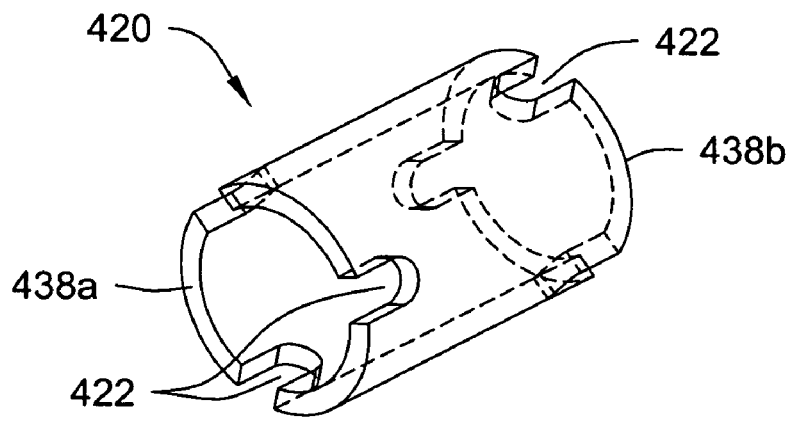
FIG. 8 is a perspective view of another example marker band for use with a medical device.

Similar to what is described above, holes or slits 322 can vary in number and arrangement. For example, FIG. 7 depicts two pairs of holes 322 (i.e., four holes 322) at each end 338a/b that are radially aligned. In addition, holes 322 are also longitudinally aligned with the corresponding holes 322 on the opposite end 338a/b of marker band 320. However, these holes could alternatively be staggered radially and/or longitudinally as well as vary in number. For example, FIG. 8 depicts marker band 420 having three holes 422 disposed at each of ends 438a/b. Holes 422 are arranged in a staggered configuration both radially and longitudinally. It can be appreciated that other embodiments of marker bands are contemplated where the holes are staggered either radially or longitudinally, but not both.

Figure 9:
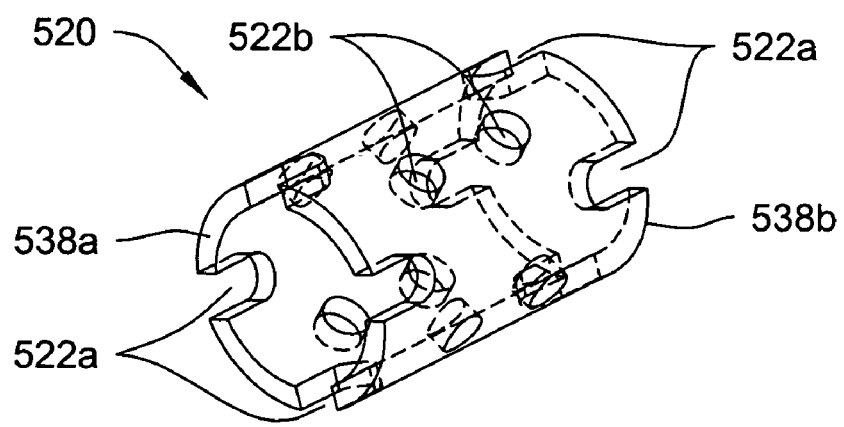
FIG. 9 is a perspective view of another example marker band for use with a medical device.

FIG. 9 depicts another example marker band 520 that is similar to the other bands described herein except that marker band 520 include holes 522a disposed at ends 538a/b and holes 522b formed medially within body 534 of marker band 520. Of course, the number, arrangement, and shape of holes 522b (as well as holes 522a) can vary as seen in the aforementioned embodiments.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device, comprising:
    a tubular member having a proximal end region and a distal end region;
    a radiopaque marker band disposed over the tubular member, the marker band having an outer surface and an inner surface with one or more openings through the outer surface of the marker band; and
    an outer layer disposed over the outer surface of the marker band, wherein the outer layer extends from the outer surface of the marker band into the openings in the marker band, completely fills the openings, and is at least partially disposed between the tubular member and the inner surface of the radiopaque marker.

2. The medical device of claim 1, wherein the openings are defined by generally circular holes formed in the marker band.

3. The medical device of claim 1, wherein the openings are defined by generally oval holes formed in the marker band.

4. The medical device of claim 1, wherein the marker band includes two or more holes.

5. The medical device of claim 4, wherein the holes are aligned on opposite sides of the marker band.

6. The medical device of claim 4, wherein on opposite sides of the marker band the holes are offset.

7. The medical device of claim 1, wherein the outer layer extends through the openings and under a portion of the inner surface of the marker band.

8. The medical device of claim 1, wherein the marker band includes a proximal end region and a distal end region, and wherein the openings are defined by one or more slits in the proximal end region, the distal end region, or both.

9. The medical device of claim 8, wherein the slits are in the proximal end region and the distal end region, and wherein the slits in the proximal end region are aligned with the slits in the distal end region.

10. The medical device of claim 8, wherein the slits are in the proximal end region and the distal end region, and wherein the slits in the proximal end region are staggered relative to the slits in the distal end region.

11. A medical device, comprising:
    a tubular member having a proximal end region and a distal end region;
    a radiopaque marker band disposed over the tubular member, the marker band having an outer surface and an inner surface with one or more openings through the outer surface of the marker band;
    an outer layer surrounding the marker band, wherein the outer layer extends from the outer surface of the marker band into the openings in the marker band, completely fills the openings, and is at least partially disposed between the tubular member and the inner surface of the radiopaque marker; and
    wherein the tubular member includes an outer surface, and wherein the outer surface is defined by a fluorocarbon polymer.

12. A medical device, comprising:
    an elongate core member having a proximal end region and a distal end region;
    a radiopaque marker band disposed over the core member, the marker band having one or more slits defined therein, the marker band having an inner surface and an outer surface; and
    a coating disposed over the outer surface of the marker band, wherein the coating extends from the outer surface of the marker band toward the core member and completely fills the one or more slits of the marker band;
    wherein the coating is at least partially disposed between the core member and the inner surface of the radiopaque marker.

13. The medical device of claim 12, wherein the core member forms a catheter shaft.

14. The medical device of claim 12, wherein the core member forms a guidewire.

15. The medical device of claim 12, wherein the coating extends through the slit of the marker band and along a portion of the inner surface of the marker band.

16. A guide catheter comprising:
   an inner tubular member having a proximal region and a distal region;
   a radiopaque marker band disposed over a portion of the inner tubular member at a selected location in the distal region, the radiopaque marker having an inner surface and an outer surface with at least one opening extending from the inner surface to the outer surface; and
   an outer layer extending over the marker band and at least a portion of the inner tubular member, wherein a portion of the outer layer extends through the at least one opening and is in contact with the inner tubular member and completely fills the at least one opening;
   wherein the outer layer is at least partially disposed between the inner tubular member and the inner surface of the radiopaque marker.

17. The guide catheter of claim 16, wherein the outer layer includes multiple segments of polymeric material having desired property variations.

18. The guide catheter of claim 16, wherein the portion of the outer layer extending through the at least one hole forms a bond to the inner tubular member.

* * * * *

UNITED STATES PATENT AND TRADEMARK OFFICE
CERTIFICATE OF CORRECTION

| | | |
|---|---|---|
| PATENT NO. | : 7,641,647 B2 | Page 1 of 1 |
| APPLICATION NO. | : 10/749499 | |
| DATED | : January 5, 2010 | |
| INVENTOR(S) | : Richard C. Gunderson | |

It is certified that error appears in the above-identified patent and that said Letters Patent is hereby corrected as shown below:

Column 5
Line 29: delete "tat" and insert therefor -- that --.

Signed and Sealed this

Ninth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,641,647 B2  Page 1 of 1
APPLICATION NO. : 10/749499
DATED : January 5, 2010
INVENTOR(S) : Richard C. Gunderson It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 774 days.

Signed and Sealed this

Sixteenth Day of November, 2010

David J. Kappos
*Director of the United States Patent and Trademark Office*